(12) United States Patent
Sharma et al.

(10) Patent No.: US 9,273,073 B2
(45) Date of Patent: Mar. 1, 2016

(54) TIN DIOXIDE NANOPARTCLES AND METHOD FOR MAKING THE SAME

(75) Inventors: Neeraj Sharma, Woodbury, MN (US); Brant U. Kolb, Afton, MN (US); Mark J. Hendrickson, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/122,095

(22) PCT Filed: May 23, 2012

(86) PCT No.: PCT/US2012/039076
§ 371 (c)(1),
(2), (4) Date: Nov. 25, 2013

(87) PCT Pub. No.: WO2013/002919
PCT Pub. Date: Jan. 3, 2013

(65) Prior Publication Data
US 2014/0135206 A1 May 15, 2014

Related U.S. Application Data

(60) Provisional application No. 61/502,181, filed on Jun. 28, 2011.

(51) Int. Cl.
*B01J 23/14* (2006.01)
*C07F 7/22* (2006.01)
*C08K 9/04* (2006.01)
*C01G 19/02* (2006.01)
*C09C 1/00* (2006.01)
*B82Y 30/00* (2011.01)

(52) U.S. Cl.
CPC .............. *C07F 7/2224* (2013.01); *B82Y 30/00* (2013.01); *C01G 19/02* (2013.01); *C08K 9/04* (2013.01); *C09C 1/00* (2013.01); *C01P 2002/50* (2013.01); *C01P 2004/64* (2013.01)

(58) Field of Classification Search
CPC ........ B01J 23/14; C07F 7/2224; B82Y 30/00; C01G 19/02; C08K 9/04; C01P 2004/64; C01P 2002/50
USPC ............................ 502/349; 977/773, 775, 811
IPC ........................................................ B01J 23/14
See application file for complete search history.

(56) References Cited

U.S. PATENT DOCUMENTS

| | | | |
|---|---|---|---|
| 5,453,262 | A | 9/1995 | Dawson |
| 5,652,192 | A | 7/1997 | Matson |
| 6,291,070 | B1 * | 9/2001 | Arpac et al. ................... 428/412 |
| 6,376,691 | B1 | 4/2002 | Celinska |
| 6,533,966 | B1 | 3/2003 | Nonninger |
| 7,160,525 | B1 | 1/2007 | Peng |
| 7,531,149 | B2 | 5/2009 | Peng |
| 7,858,195 | B2 * | 12/2010 | Aslan et al. ................... 428/446 |
| 2008/0166289 | A1 * | 7/2008 | Meyer et al. ................. 423/594.9 |
| 2009/0004098 | A1 * | 1/2009 | Schmidt et al. ................ 423/608 |
| 2011/0036269 | A1 * | 2/2011 | Hill et al. .................. 106/287.19 |
| 2013/0187104 | A1 * | 7/2013 | Shiraishi et al. ........... 252/520.1 |

FOREIGN PATENT DOCUMENTS

| | | |
|---|---|---|
| CN | 1775693 | 5/2006 |
| EP | 1990395 | 11/2008 |
| KR | 2005-004578 | 1/2005 |
| KR | 2006-113133 | 11/2006 |
| WO | WO 2005-049520 | 6/2005 |
| WO | WO 2008-058849 | 5/2008 |
| WO | WO 2009-085926 | 7/2009 |

OTHER PUBLICATIONS

Adschiri, "Rapid and Continuous Hydrothermal Crystallization of Metal Oxide Particles in Supercritical Water", Journal of American Ceramic Society, Apr. 1992, vol. 75, No. 4, pp. 1019-1022.

Aegerter, "Comparative study of $SnO_2$:Sb transparent conducting films produced by various coating and heat treatment techniques", Journal of Non-Crystalline Solids, Sep. 1997, vol. 218, pp. 123-128.

Ba,"Crystallization of Indium Tin Oxide Nanoparticles: From Cooperative Behavior to Individuality", Small, Feb. 2007, vol. 3, No. 2, pp. 310-317.

Bernardi, "Influence of the concentration of $Sb_2O_3$ and the viscosity of the precursor solution on the electrical and optical properties of $SnO_2$ thin films produced by the Pechini method", Thin Solid Films, 2002, vol. 405, pp. 228-233.

Bommel, "The electrical and optical properties of thin layers of nano-sized antimony doped tinoxide particles", Journal of Materials Science, 1999, vol. 34, No. 19, pp. 4803-4809.

Chopra, "Transparent conductors—A status review", Thin Solid Films, 1983, vol. 102, No. 1, pp. 1-46.

Dawson, "Hydrothermal synthesis of advanced ceramic powders", American Ceramic Society Bulletin, 1988, vol. 67, No. 10, pp. 1673-1678.

De Melo, "Thermal and structural investigation of $SnO_2/Sb_2O_3$ obtained by the polymeric precursor method", Journal of Thermal Analysis Calorimetry, Mar. 2007, vol. 87, No. 3, pp. 697-701.

Dyshel, "Effect of heat treatment on the dispersity of Sn(IV)-Sb-O powders and the porosity of thick-film gas sensors based on them", Powder Metallurgy and Metal Ceramics, 1999, vol. 38, No. 5-6, pp. 309-313.

(Continued)

*Primary Examiner* — Patricia L Hailey
(74) *Attorney, Agent, or Firm* — Qiang Han

(57) ABSTRACT

Plurality of crystalline, surface modified tin oxide nanoparticles, wherein the particles have a largest dimension up to 20 nm, and wherein the surface modifier comprises at least one of an organic carboxylic acid or anion thereof, including a dispersion comprising the crystalline, surface modified tin oxide nanoparticles and methods to make the same. The crystalline surface modified doped tin oxide nanoparticles are useful, for example, for preparing transparent electrodes, heat mirrors and energy storage devices.

12 Claims, No Drawings

(56) References Cited

OTHER PUBLICATIONS

Endo, "Direct Preparation and Size Control of Highly Crystalline Cubic ITO Nanoparticles in a Concentrated Solution System", Chemistry Letters, 2008, vol. 37, No. 12, pp. 1278-1279.
Epifani, "Synthesis and Gas-Sensing Properties of Pd-Doped $SnO_2$ Nanocrystals. A Case Study of a General Methodology for Doping Metal Oxide Nanocrystals", Crystal Growth and Design, 2008, vol. 8, No. 5, pp. 1774-1778.
Franke, "Metal and Metal Oxide Nanoparticles in Chemiresistors: Does the Nanoscale Matter?", Small, 2006, vol. 2, No. 1, pp. 36-50.
Ganz, "Laser Sintering of SnO2 : Sb Sol-Gel Coatings", Journal of Sol-Gel Science and Technology, 1998, vol. 13, No. 1-3, pp. 961-967.
Gasparro, "$SnO_2$: Sb transparent conducting coatings made by different sol-gel processes", Proceedings of SPIE, SolGel Optics IV Oct. 1997, vol. 3136, pp. 407-418.
Geraldo, "Drude's model calculation rule on electrical transport in Sb-doped $SnO_2$ thin films, deposited via sol-gel", Journal of Physics and Chemistry of Solids, 2006, vol. 67, No. 7, pp. 1410-1415.
Gilstrap, "Synthesis of a Nonagglomerated Indium Tin Oxide Nanoparticle Dispersion", Advanced Materials, Nov. 2008, vol. 20, No. 21, pp. 4163-4166.
Giraldi, "Effect of Thickness on the Electrical and Optical Properties of Sb Doped $SnO_2$ (ATO) Thin Films", Journal of Electroceramics, 2004, vol. 13, No. 1-3, pp. 159-165.
Goebbert, "Ultrafiltration conducting membranes and coatings from redispersable, nanoscaled, crystalline $SnO_2$:Sb particles", . Journal of Materials Chemistry, 1999, vol. 9, pp. 253-258.
Goebbert, "Wet Chemical Deposition of Crystalline, Redispersable ATO and ITO Nanoparticles", Journal of Sol-Gel Science and Technology, 2000, vol. 19, No. 1-3, pp. 201-204.
Grzeta, "Structural studies of nanocrystalline $SnO_2$ doped with antimony: XRD and Mossbauer spectroscopy" Journal of Physics and Chemistry of Solids, 2002, vol. 63, pp. 765-772.
Hagemeyer, "High surface area tin oxide", Applied Catalysis, A: General, Feb. 2007, vol. 317, No. 2, pp. 139-148.
Hu, "Preparation and characterization of Sb-doped $SnO_2$ thin films from colloidal precursors", Material Chemistry Physics, 2004, vol. 86, pp. 21-25.
International Searh Report for PCT International Application No. PCT/US2012/039076, Mailed on Jul. 27, 2012, 3 pages.
Iwasaki, "Synthesis of nanometer-sized SnOx particles by NAS-FAS method and their electric conductivity", Shikizai Kyokai shi, 2000, vol. 73, No. 11, pp. 535.
Jeon, "Synthesis and characterization of antimony-doped tin oxide (ATO) with nanometer-sized particles and their conductivities", Materials Letters, Jun. 2005, vol. 59, No. 14-15, pp. 1801-1810.
Jung, "Synthesis of nano-sized antimony-doped tin oxide (ATO) particles using a DC arc plasma jet", Applied Surface Science, 2009, vol. 255, pp. 5409-5413.
Kappler, "Correlation between XPS, Raman and TEM measurements and the gas sensitivity of Pt and Pd doped SnO2 based gas sensors", Fresenius Jounal of Analytical Chemistry, 1998, vol. 361, No. 2, pp. 110-114.

Leite, "The effect of Sb and Nb on the electrical conductivity of tin dioxide based ceramics", Journal of Materials Science, 2006, vol. 41, No. 19, pp. 6256-6259.
Matsushima, " Role of additives on alcohol sensing be semiconductor gas sensor", Chemistry Letters, 1989, vol. 18, pp. 845-848.
Nutz, "Wet-chemical synthesis of doped nanoparticles: Blue-colored colloids of $n$-doped $SnO_2$:Sb", Journal of Chemical Physics, Jun. 1999, vol. 110, No. 24, pp. 12142-12150.
Nutz, "Wet-Chemical Synthesis of Doped Nanoparticles: Optical Properties of Oxygen-Deficient and Antimony-Doped Colloidal $SnO_2$", Journal of Physical Chemistry B, 2000, vol. 104, No. 35, pp. 8430-8437.
Sakai, "Gas sensing properties of tin oxide thin films fabricated from hydrothermally treated nanoparticles. Dependence of CO and $H_2$ response on film thickness", Sensors and Actuators B, 2001, vol. 77, pp. 116-121.
Scherrer, "Determination of the Size and Internal Structure of Colloid Particles", presented at Göttingen Physical Institute, Jul. 26, 1918, 5 pages.
Shimizu, "Basic Aspects and Challenges of Semiconductor Gas Sensors", MRS Bulletin, 1999, vol. 24, No. 6, pp. 18-24.
Shimizu, "Effects of gas diffusivity and reactivity on sensing properties of thick film $SnO_2$-based sensors", Sensors and Actuators B: Chemical, 1998, vol. 46, No. 3, pp. 163-168.
Tiemann, "Porous Metal Oxides as Gas Sensors", Chemistry—A European Journal, 2007, vol. 13, No. 30, pp. 8376-8388.
Williams, "Reaction-diffusion effects and systematic design of gas-sensitive resistors based on semiconducting oxides", Journal of the Chemical Society Faraday Transactions, 1995, vol. 91, No. 23, pp. 4299-4307.
Xu, "Grain size effects on gas sensitivity of porous $SnO_2$-based elements", Sensors and Actuators B: Chemical, 1991, vol. 3, No. 2, pp. 147-155.
Yamazoe, "New approaches for improving semiconductor gas sensors" Sensors and Actuators B: Chemical, 1991, vol. 5, No. 1-4, pp. 7-19.
Yamazoe, "Oxide Semiconductor Gas Sensors" Catalysis Surveys from Asia, Apr. 2003, vol. 7, No. 1, pp. 63-75.
Yamazoe, "Roles of Shape and Size of Component Crystals in Semiconductor Gas Sensors", Journal of the Electrochemical Society, Jan. 2008, vol. 155, No. 4, pp. J85-J92.
Yamazoe, "Roles of Shape and Size of Component Crystals in Semiconductor Gas Sensors", Journal of the Electrochemical Society, Jan. 2008, vol. 155, No. 4, pp. J93-J98.
Zhang, "A novel solvothermal method to synthesize one-dimensional chains of indium tin oxide nanoparticles", Materials Letters, May 2007, vol. 61, No. 13, pp. 2671-2674.
Zhang, "Shape-Controlled Synthesis of Zinc Oxide: A Simple Method for the Preparation of Metal Oxide Nanocrystals in Non-aqueous Medium", Chemistry—A European Journal, Jan. 2007, vol. 13, No. 2, pp. 632-638.
Zhu, "Sol-Gel-Derived Sb-Doped $SnO_2$ Nanoparticles Controlled in Size by $Nb_2O_5$,", Chemical Engineering Technology, Oct. 2003, vol. 26, No. 10, pp. 1084-1087.

\* cited by examiner

TIN DIOXIDE NANOPARTCLES AND METHOD FOR MAKING THE SAME

CROSS REFERENCE TO RELATED APPLICATIONS

This application is a national stage filing under 35 U.S.C. 371 of PCT/US2012/039076, filed May 23, 2012, which claims priority to U.S. Provisional Application No. 61/502, 181, filed Jun. 28, 2011, the disclosure of which is incorporated by reference in its/their entirety herein.

BACKGROUND

Tin oxide ($SnO_2$) is known to be useful for gas sensor applications due to its relatively high gas sensitivity, good stability, and low cost. Crystallite size, microstructure, and surface modification (noble metal loading) play a role in the gas-sensing properties of $SnO_2$. Among these, decreasing the crystalline size of $SnO_2$ is quite effective in improving its gas sensitivity. Tin oxide grains contained in gas sensors typically are <20 nm and stable from thermal growth during the sensing operation at elevated temperatures (300° C.-600° C.). These requirements have been met for sensor devices of the sintered block or thick-film types. Thin film tin oxide sensor fabrication by spin-coating or dip-coating from a colloidal suspension, or sol, of tin oxide has provided films with higher sensitivity and stability.

Doping of tin dioxide with other metal ions results in electronic materials with several desirable properties. One of the most prominent of the doped Tin dioxide materials is antimony-doped tin oxide (ATO). The introduction of antimony (Sb) into the tin oxide lattice is reported to greatly increase the electron conductivity, which renders this material useful as an excellent conductive agent. ATO is transparent throughout the visible region, but reflects/absorbs infrared light. These features make the ATO useful, for example, as transparent electrodes, heat mirrors, and energy storage devices. Surface modified ATO nanoparticles can be combined with a variety of polymeric resins to create optically clear nanocomposites film or laminates which are heat shielding. Nanoparticulate ATO has also been used as electrochromic material for the production of printed displays and anode material in lithium-ion batteries. In addition, ATO has applications in nuclear waste management and is a good catalyst for olefin oxidation.

Tantalum and niobium doped tin dioxide materials display nonlinear electrical properties and are useful as varistor materials.

The preparation of doped tin oxide nanoparticles with different shape, size, conductivity, and degree of agglomeration has been addressed by a large variety of techniques. Top-down milling process of agglomerated nanopowders of doped or undoped tin oxide are energy and time intensive and generating nanoparticles <50 nm is difficult to achieve. Smaller particle size of the nanoparticle can improve the optical clarity and decrease the haze of the final product.

Chemical methods in general can provide nanoparticles with smaller size in form of stable dispersions than the physical methods. The sol-gel, polymeric precursor, and co-precipitation techniques mostly provide either large particles or nanoparticle agglomerates. Calcination steps involved in some of these processes accelerate growth and agglomeration of obtained particle. Much better control over the growth of doped tin oxide particles has been achieved by hydrothermal and solvothermal techniques.

The hydrothermal method does not need a calcination process, and the dispersibility of the particles is greatly improved. The starting materials used in the hydrothermal methods are often soluble metal chloride, nitrate or sulfate salts. In the case of tin $SnCl_4$, $SnCl_4.5H_2O$, $SnCl_2$, or $SnCl_2.2H_2O$, are commonly used halide precursors where as for antimony $SbCl_3$ and $SbCl_5$ are used. Chlorine has been known to get adsorbed on tin hydroxide and is very difficult to remove, and large amount of product is lost during the repeated washing. The residual chlorine ions also affect the surface and electrical properties. In addition these salts are also corrosive and precautions are needed to avoid contamination or corrosion of stainless steel reactors. New synthetic processes involving benign precursors would be desirable for improving the yield and quality of doped and undoped tin oxide nanoparticles. Dispersions of the nanoparticles instead of agglomerated powders could also decrease post-synthesis processes needed to include them in nanocomposites.

There is a need for a process to prepare doped and undoped tin oxide nanoparticles as a stable dispersion with primary particle sizes <20 nm without the limitation of known processes.

SUMMARY

In one aspect, the present disclosure describes a plurality of crystalline, surface modified tin oxide nanoparticles, wherein the particles have a largest dimension up to 20 nm (in some embodiments, up to 15 nm, 10 nm, 5 nm, 3 nm, or even up to 2 nm; in some embodiments, in a range from 1 nm to 20 nm, 1 nm to 15 nm, 1 nm to 10 nm, 2 nm to 20 nm, 2 nm to 15 nm, 2 nm to 10 nm, 3 nm to 20 nm, 3 nm to 15 nm, or even 3 nm to 10 nm), and wherein the surface modifier comprises at least one of a organic carboxylic acid or anion thereof. In some embodiments, the crystalline, surface modified tin oxide nanoparticles further comprise at least one of a metal or metal oxide dopant (e.g., aluminum, gallium, antimony, indium, bismuth, lead, transition metal (i.e., Ti, V, Cr, Mn, Fe, Co, Ni, Cu, Zn, Zr, Nb, Mo, Ru, Rh, Pd, Ag, Cd, Hf, Ta, W, Re, Ir, Pt, and/or Au) and/or lanthanide (i.e., La, Ce, Pr, Nd, Sm, Eu, Gd, Tb, Dy, Ho, Er, Tm, Yb, and/or Lu)).

In another aspect, the present disclosure describes a dispersion comprising a plurality of crystalline, surface modified tin oxide nanoparticles described herein.

In another aspect, the present disclosure describes a method of making a embodiments of method of making a plurality of crystalline, surface modified tin oxide nanoparticles described herein, the method comprising:

providing a solution preparable by combining at least a tin carboxylate, water, and carboxylic acid, wherein the carboxylic acid to water mole ratio is at least 2:1 (in some embodiments, at least 3:1, 4:1, 5:1, 10:1, or even at least 15:1; in some embodiments, in a range from 3.5:1 to 1.5:1), and wherein the water to tin carboxylate plus dopant mole ratio is at least 1.3:1 (in some embodiments, at least 2:1, 3:1, 3:1, 4:1, 5:1, or even at least 8:1; in some embodiments, in a range from 1.3:1 to 8.25:1); and heating the solution to at least one temperature for a time sufficient to provide the crystalline, surface modified tin oxide nanoparticles.

In another aspect, the present disclosure describes a method of making a embodiments of plurality of crystalline, surface modified tin oxide nanoparticles described herein, the method comprising:

providing a solution preparable by combining at least a tin carboxylate, a dopant precursor comprising at least one of antimony, indium, silver, bismuth, lead, transition metal, or lanthanide, water, and carboxylic acid, to provide the solution, wherein a sufficient amount of water is present to dissolve the dopant precursor and metal carboxylate; and heating the solution to at least one temperature for a time sufficient to provide the crystalline, surface modified tin oxide nanoparticles.

Crystalline, surface modified tin oxide nanoparticles described herein are useful, for example, for preparing transparent electrodes, heat mirrors, and energy storage devices.

DETAILED DESCRIPTION

Crystalline, surface modified tin oxide nanoparticles described herein can be made, for example, by preparing a feedstock solution by combining at least a tin carboxylate, water and carboxylic acid, wherein the carboxylic acid to water mole ratio is at least 2:1 (in some embodiments, at least 3:1, 4:1, 5:1, 10:1, or even at least 15:1; in some embodiments, in a range from 3.5:1 to 1.5:1), and wherein the water to tin carboxylate plus dopant mole ratio is at least 1.3:1 (in some embodiments, at least 2:1, 3:1, 3:1, 4:1, 5:1, or even at least 8:1; in some embodiments, in a range from 1.3:1 to 8.25:1) and subjecting it to a hydro-solvothermal treatment. The amount of water is at least sufficient to dissolve the metal (e.g., tin) carboxylate present. Typically, the carboxylic acid to water mole ratio is in a range from 2.8:1 to 15.6:1 (in some embodiments, in a range from 2:1 to 15:1, 2:1 to 13:1, 2:1 to 10:1, 2:1 to 8:1, 2:1 to 5:1, or even 3:1 to 4:1).

As used herein, the term "hydro-solvothermal" refers to a method of heating an aqueous and non-aqueous solvent mixture to a temperature above the normal boiling point of the aqueous medium at a pressure that is equal to or greater than the pressure required to prevent the boiling of the aqueous/solvent medium.

Typically, the tin carboxylate present in the feedstock solution has no greater than 4 carbon atoms. Suitable carboxylates include formate, acetate, propionate (i.e., n-propionate), butyrate (i.e., n-butyrate, iso-butyrate, or a mixture thereof), and combinations thereof. Exemplary tin carboxylates include tin formate, tin acetate, tin propionate, tin butyrate and mixtures thereof.

Typically, the corresponding carboxylic acids of these carboxylates are also present in the feedstock along with sufficient amounts of water and tin carboxylate. The carboxylic acid in the feedstock typically has no greater than 4 carbon atoms as such small chain organocarboxylate groups on the surface of the nanoparticles have been observed to facilitate of the exchange with other carboxylic acids in order to alter the surface property and compatibility with solvents and resins with varying polarity.

Exemplary carboxylic acids include acetic acid, formic acid, propionic acid, butyric acid, and mixtures thereof.

The feedstock solution is usually free or substantially free of any carboxylate and/or acid thereof that has greater than 4 carbon atoms (i.e., in the case of the latter, less than 1 mole percent, (in some embodiments, less than 0.5 mole percent, 0.3 mole percent, 0.2 mole percent, 0.1 mole percent, 0.05 mole percent, 0.02 mole percent, or even less than 0.01 mole percent of carboxylate and/or acid thereof).

The tin precursor in the feedstock solution are typically tin carboxylate salts selected to be removable during subsequent processing steps and to be non-corrosive (as opposed to, for example, tin chloride salts, tin sulfate salts, and tin nitrate salts). Free Halide, sulfate and nitrate anions are desirable not present or removed in the subsequent processing steps as they can result in the formation of undesired corrosive acids. In some instances, halide anions have been also known to accumulate in the tin oxide nanoparticle and undesirably influence its electronic properties, however, there are other applications where presence of halide, nitrate or sulfate anions in residual amounts may not have such a deleterious effect (e.g., in uses such as IR reflective films or coatings). Further, carboxylates and/or acids thereof tend to be more compatible with an organic matrix material compared to halides and nitrates. Many tin precursors used to prepare the feedstock solutions are free or substantially free of halides, sulfates and nitrates (i.e., in the case of the latter, no greater than 30 millimolar, 25 millimolar, 20 millimolar, 15 millimolar, 10 millimolar, 5 millimolar, 1 millimolar, or even no greater than 0.5 millimolar halide, nitrate and/or sulfate).

The tin carboxylate salt is often a tin acetate salt. Tin Acetate can be represented by $Sn^{II}(CH_3COO)_2$, where tin is in +2 oxidation state or $Sn^{IV}(CH_3COO)_4$, and where tin is in +4 oxidation state. Both tin (II) acetate and tin (IV) acetate are commercially available from a variety of manufacturers. Other tin acetates can contain tin atom in an average oxidation state between +2 and +4, where the average oxidation state is calculated by sum of the oxidation states of all tin atoms divided by the number of tin atoms. Some tin carboxylates can contain oxide and/or hydroxide ligand in addition to carboxylates.

The feedstock solution is subjected to a hydro-solvothermal treatment. The dissolved tin species in the feedstock solution undergo hydrolysis (water is essential component of the feedstock solution) and condensation to form a tin oxide nanoparticle.

The hydrothermal-solvothermal treatment can be, for example, in a batch reactor or in a continuous reactor. The heating times are typically shorter and the temperatures are typically higher in a continuous hydrothermal reactor compared to a batch hydro-solvothermal reactor. The time of the hydro-solvothermal treatment can be varied depending, for example, on the type of the reactor, the temperature of the reactor, and the concentration of the feedstock. The pressure in the reactor can be, for example, autogeneous (i.e., the vapor pressure of water-solvent mixture at the temperature of the reactor), hydraulic (i.e., the pressure caused by the pumping of a fluid against a restriction), or can result from the addition of an inert gas such as nitrogen or argon. Suitable batch hydrothermal reactors are available, for example, from Parr Instruments Co., Moline, Ill. Some suitable continuous hydrothermal reactors are described, for example, in U.S. Pat. No. 5,453,262 (Dawson et. al.) and U.S. Pat. No. 5,652,192 (Matson et. al.); Adschiri et. al., *J. Am. Ceram. Soc.*, 75, 1019-1022 (1992); and Dawson, *Ceramic Bulletin*, 67 (10), 1673-1678 (1988).

The hydro-solvothermal treatment of the feedstock solution is carried out to at least one temperature (e.g., 150° C. to 275° C. (in some embodiments, in a range from 150° C. to 250° C.) for a time (e.g., 225° C. for 4 hours) sufficient to provide the crystalline, surface modified tin oxide nanoparticles. If the temperature if greater than 275° C. the pressure may be unacceptably high for some hydrothermal reactor systems. However, if the temperature is lower than 150° C., the conversion of tin precursor to tin oxide nanoparticle may not be complete unless the reaction times are very long instead of few hours at moderately high temperatures of 225° C.

In embodiments wherein the crystalline, surface modified tin oxide nanoparticles include a dopant, at least a sufficient amount of water is present to dissolve the dopant metal and tin carboxylate. For these embodiments, the water to tin carboxylate plus dopant mole ratio is typically in a range from 1.3:1 to 8.25:1 (in some embodiments, in a range from 2:1 to 8:1, 3:1 to 8:1, 4:1 to 8:1, 5:1 to 8:1, or even 6:1 to 7:1).

The largest dimension of the nanoparticles is up to 20 nm. In some embodiments, the largest dimension of the nanoparticles is up to 15 nm, 10 nm, 5 nm, 3 nm, or even up to 2 nm; in some embodiments, in a range from 1 nm to 20 nm, 1 nm to 15 nm, 1 nm to 10 nm, 2 nm to 20 nm, 2 nm to 15 nm, 2 nm to 10 nm, 3 nm to 20 nm, 3 nm to 15 nm, or even 3 nm to 10 nm.

In some embodiments, the crystalline, surface modified tin oxide nanoparticles comprise up to 20 (in some embodiments, up to 15, 10, 5, 4, 3, 2, 1, or even up to 0.5; in some embodiments, in a range from greater than zero to 20 to 1 to 20, 5 to 20, or even 10 to 15) atom percent of dopant.

Exemplary dopants include at least one a metals or metal oxide of at least one of aluminum, gallium, antimony, indium, bismuth, lead, transition metal (i.e., Ti, V, Cr, Mn, Fe, Co, Ni, Cu, Zn, Zr, Nb, Mo, Ru, Rh, Pd, Ag, Cd, Hf, Ta, W, Re, Ir, Pt, and/or Au) or lanthanide (i.e., La, Ce, Pr, Nd, Sm, Eu, Gd, Tb, Dy, Ho, Er, Tm, Yb, and/or Lu).

Exemplary dopant precursors include metal carboxylates salts selected to be non-corrosive and removable during subsequent processing steps. At least a majority by mole of the dopant precursor salts in the feedstock are usually carboxylate salts rather than halide salts, oxyhalide salts, nitrate salts, and/or oxynitrate salts. Halide anions in the feedstock tend to results in either accumulation in the nanoparticle structure which can impact the electronic property of the doped nanoparticle or the formation of free halide ions which are typically removed in subsequent processing steps from the final nanoparticle dispersion. Further, carboxylates and/or acids thereof tend to be more compatible with an organic matrix material compared to halides and nitrates. Although any carboxylate anion can be used, the carboxylate anion often has no greater than 4 carbon atoms (e.g., formate, acetate, propionate, butyrate, and combinations thereof). Often carboxylate anions are provided by dissolving salts (e.g., often acetate salts). The feedstock may, for example, further include the corresponding carboxylic acid of the carboxylate anion. For example, feedstocks prepared from acetate salts often contain acetic acid. Because the dopant salts are typically used at much lower concentration levels than the tin salt, however, salts other than carboxylate salts (e.g., acetate salts) are more easily used. For example, any of these salts can be a nitrate salt.

Many dopant precursors used to prepare the feedstock solutions are free or substantially free of halides, sulfates and nitrates (i.e., in the case of the latter, less than 1 mole percent, 0.5 mole percent, 0.3 mole percent, 0.2 mole percent, 1 mole percent, 0.05 mole percent, 0.02 mole percent, or even less than 0.01 mole percent of halides, sulfates and/or nitrates).

The dopant metal carboxylate salt is often a metal acetate salt. The metal in a dopant metal acetate can exist in many oxidation states. Dopant metal acetates can be, for example, anhydrous or hydrated salts. Dopant metal atom in the doped tin dioxide can exist in more than one oxidation states. Dopant metals can also influence the oxidation state of tin in tin oxide nanoparticles. Several dopant metal carboxylates including metal acetates are commercially available from a variety of manufacturers. Some dopant metal carboxylates can contain oxide and/or hydroxide or halide ligands in addition to carboxylates (e.g., zirconyl acetate and dibasic aluminum acetate stabilized with boric acid).

The total amount of the various salts dissolved in the feedstock can be readily determined based on the total percent solids selected for the feedstock. The relative amounts of the various salts can be calculated to provide the selected composition for the tin oxide-based particles.

The feedstock solution is subjected to a hydro-solvothermal treatment. The dissolved tin and dopant metal species in the feedstock solution undergo hydrolysis (water is essential component of the feedstock solution) and condensation to form a doped tin oxide nanoparticle.

The effluent of the hydro-solvothermal treatment (i.e., the product of the hydro-solvothermal treatment) contains doped or undoped tin oxide nanoparticle depending on the presence of dopant precursor along with tin precursor. More, particularly the effluent of the hydro-solvothermal treatment is a tin-containing sol. As used herein, the term "sol" refers to a dispersion or suspension of the tin or tin and dopant-containing nanoparticles in a mixed aqueous-based medium.

In some embodiments, at least a portion of the aqueous-based acid medium is removed from the tin or tin and dopant-containing sol. Any known technique for removing the aqueous-based medium can be used. This aqueous-based medium contains water and dissolved carboxylic acids and/or anions thereof that are present in the feedstock solutions or that are byproducts of the reactions that occur within the hydrothermal reactor. As used herein, the term "carboxylic acids and/or anions thereof" refers to carboxylic acids, carboxylate anions of these carboxylic acids, or mixtures thereof. The removal of at least a portion of these dissolved carboxylic acids and/or anions thereof from tin or tin and dopant-containing sol may be desirable in some applications. The tin or tin and dopant-containing sol can be subjected to methods such as vaporization, drying, ion-exchange, solvent exchange, diafiltration, or dialysis.

In some embodiments, the effluent of the hydrothermal reactor is concentrated or dried with a drying process. Along with removing at least a portion of the water present in the effluent, the concentration process often results in the vaporization of at least a portion of the dissolved carboxylic acids. Any suitable drying methods can be used such as spray drying, gap drying, or oven drying. For example the effluent can be dried in a conventional oven at a temperature of at least 80° C.

In some embodiments, the effluent of the hydrothermal treatment is subjected to a solvent exchange process. An organic solvent with a higher boiling point than the water and carboxylic acid present in the sol can be added to the effluent. The mixture containing the effluent plus the organic solvent can be treated to remove the water using methods such as, for example, distillation, rotary evaporation, or oven drying. Often, at least a portion of the dissolved carboxylic acids can be removed along with the water.

The effluent of the hydro-solvothermal treatment usually contains non-aggregated doped or undoped tin oxide nanoparticles. The undoped tin oxide sol is typically clear and colorless, whereas doped tin oxide sol is clear but can have color which depends on dopant and tin oxidation state. In contrast both undoped and doped tin oxide sols containing agglomerated or aggregated particles tend to have a milky or cloudy appearance. Both undoped and doped tin oxide sols often have a high optical transmission due to the small size and lack of substantial aggregation of the tin oxide particles in the sol. High optical transmission of the sol can be desirable in the preparation of transparent or translucent composite materials. As used herein, "optical transmission" refers to the amount of light that passes through a sample (e.g., tin oxide sol) divided by the total amount of light incident upon the sample. The percent optical transmission may be calculated using the equation $$100(I/I_0)$$

where I is light intensity passing through the sample and $I_0$ is light intensity incident on the sample. The optical transmission may be determined by using a spectrophotometer set at a wavelength of 600 nm with a 1 cm path length. The optical transmission is a function of the amount of tin and dopant in the oxide sol.

In some examples undoped and doped tin oxide sol can be dried to form a powder. The powder can then be suspended or dispersed in water or organic solvent.

In some embodiments, the dried crystalline, surface modified tin oxide nanoparticles described herein are dispersible, wherein "dispersible" means the dried nanoparticles can be dispersed in an aqueous and/or organic solvent to provide a stable dispersion. A "stable dispersion" has less than 10 percent (in some embodiments, less than 5 percent, or even less than 3 percent) settling of the nanoparticles over a period of 4 days, wherein the sedimentation percentage is by weight, based upon the total weight of nanoparticles in the dispersion).

To prepare some composite materials, the doped or undoped tin oxide particles are further treated with a surface modification agent to improve compatibility with the organic matrix material. Surface modification agents may be represented by the formula A-B where the A group is capable of attaching to the surface of a tin oxide-based particle and B is a compatibility group. Group A can be attached to the surface by adsorption, formation of an ionic bond, formation of a covalent bond, or a combination thereof. Group B can be reactive or non-reactive and often tends to impart characteristics to the tin oxide-based particles that are compatible (i.e., miscible) with an organic solvent, with another organic matrix material (e.g., monomer, oligomers, and polymeric material), or both. For example, if the solvent is non-polar, group B is typically selected to be non-polar as well. Suitable B groups include linear or branched hydrocarbons that are aromatic, aliphatic, or both aromatic and aliphatic. The surface modifying agents include carboxylic acids and/or anions thereof, sulfonic acids and/or anions thereof, phosphoric acids and/or anions thereof, phosphonic acids, and/or anions thereof, silanes, amines, and alcohols. Suitable surface modification agents are further described in PCT Application Publication WO 2009/085926 (Kolb et al.), which is incorporated herein by reference.

In some embodiments, the surface modification agent is a carboxylic acid and/or anion thereof and the compatibility B group can impart a polar character to the doped or undoped tin oxide nanoparticles. For example, the surface modification agent can be a carboxylic acid and/or anion thereof having a polyalkylene oxide group. In some embodiments, the carboxylic acid surface modification agent is of the following formula.

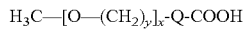

$H_3C-[O-(CH_2)_y]_x-Q-COOH$

In this formula, Q is a divalent organic linking group, x is an integer in the range of 1 to 10, and y is an integer in the range from 1 to 4. The group Q is often an alkylene group, alkenylene group, arylene, oxy, thio, carbonyloxy, carbonylimino, and combinations thereof. Representative examples of this formula, include 2-[2-(2-methoxyethoxy)ethoxyacetic acid (MEEAA) and 2-(2-methoxyethoxy)acetic acid (MEAA). Other representative examples are the reaction product of an aliphatic or aromatic anhydride and a polyalkylene oxide mono-ether such as succinic acid mono-[2-(2-methoxy-ethoxy)-ethyl]ester, maleic acid mono-[2-(2-methoxy-ethoxy)-ethyl]ester, and glutaric acid mono-[2-(2-methoxy-ethoxy)-ethyl]ester.

Still other carboxylic acid surface modifying agents are the reaction product of phthalic anhydride with an organic compound having a hydroxyl group. Suitable examples include phthalic acid mono-(2-phenylsulfanyl-ethyl) ester, phthalic acid mono-[2-(2-methoxy-ethoxy)-ethyl]ester. In some examples, the organic compound having a hydroxyl group is a hydroxyl alkyl (meth)acrylate (e.g., hydroxyethyl (meth)acrylate, hydroxypropyl (meth)acrylate, and hydroxybutyl (meth)acrylate). Examples include succinic acid mono-(2-acryloyloxy-ethyl)ester, maleic acid mono-(2-acryloyloxy-ethyl)ester, phthalic acid mono-(2-acryloyloxy-ethyl)ester, and phthalic acid mono-(2-acryloyloxy-butyl)ester. Still others include mono-(meth)acryloyloxy polyethylene glycol succinate and the analogous materials made from maleic anhydride, glutaric anhydride, and phthalic anhydride.

In some embodiments, the surface modification agent is the reaction product of polycaprolactone and succinic anhydride.

In some embodiments, the surface modification agent is a carboxylic acid and/or anion thereof, and the compatibility B group can impart a non-polar character to the doped or undoped tin oxide nanoparticles. For example, the surface modification agent can be a carboxylic acid and/or anion thereof having a linear or branched aromatic group or aliphatic hydrocarbon group. Representative, examples include octanoic acid, dodecanoic acid, stearic acid, oleic acid, and combinations thereof.

In some embodiments, the surface modification agent is a carboxylic acid and/or anion thereof, and the compatibility B group can be reactive with a polymerizable organic matrix (e.g., the B group contains a polymerizable group). Reactive carboxylic acid surface modifying agents (e.g., carboxylic acids with polymerizable groups) include acrylic acid, methacrylic acid, beta-carboxy-ethyl acrylate, mono-2-(methacryloyloxyethyl)succinate, and combinations thereof. A useful surface modification agent that can impart both polar character and reactivity to either the doped or undoped tin oxide nanoparticles is mono(methacryloyloxypolyethyleneglycol) succinate. This material may be particularly suitable for addition to the radiation curable acrylate and/or methacrylate organic matrix materials.

Exemplary silanes include alkyltrialkoxylsilanes (e.g., n-octyltrimethoxysilane, n-octyltriethoxysilane, isooctyltrimethoxysilane, dodecyltrimethoxysilane, octadecyltrimethoxysilane, propyltrimethoxysilane, and hexyltrimethoxysilane); methacryloxyalkyltrialkoxysilanes or acryloxyalkyltrialkoxysilanes (e.g., 3-methacryloxy propyltrimethoxysilanes, 3-acryloxypropyltrimethoxysilane, and 3-(methacryloxy)propyltriethoxysilane); methacryloxyalkylalkyldialkoxysilanes or acryloxyalkylalkyldialkoxysilanes (e.g., 3-(methacryloxy)propylmethyldimethoxysilane, and 3-(acryloxypropyl)methyldimethoxysilane); methacryloxyalkyldialkylalkoxysilanes or acryloxyalkyldialkylalkoxysilanes (e.g., 3-(methacryloxy)propyldimethylethoxysilane); mercaptoalkyltrialkoxylsilanes (e.g., 3-mercaptopropyltrimethoxysilane); aryltrialkoxysilanes (e.g., styrylethyltrimethoxysilane, phenyltrimethoxysilane, phenyltriethoxysilane, and p-tolyltriethoxysilane); vinyl silanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropxysilane, vinyltriphenoxysilane, vinyltri-t-butoxysilane. Vinyltris (isobutoxy)silane, vinyltriisopropenoxysilane, and vinyltris (2-methoxyethoxy)silane); 3-glycidoxypropyltrialkoxysilane (e.g., glycidoxypropyltrimethoxysilane); polyether silanes (e.g., N-(3-triethoxysilylpropyl)methoxyethoxyethoxyethyl carbamate (PEG3TES), N-(3-triethoxysilylpropyl)methoxyethoxyethoxyethyl carbamate (PEG2TES), and polyalkylene oxide alkoxysilane, a silane coupling agent that is commercially available from Momentive, Columbus, Ohio under the trade designation "SILQUEST A1230"); and combinations thereof.

Known methods of adding the surface modification agent to the tin oxide-based particles can be used. The surface modification agent can be added before or after any removal of at least a portion of the carboxylic acids and/or anions thereof from the tin oxide-based sol. The surface modification agent can be added before or after removal of the water and/or solvent from the tin oxide-based sol. The organic matrix can be added after surface modification or simultaneously with surface modification. Various methods of adding the surface modification agent are further described, for example, in WO 2009/085926 (Kolb et al.), which is incorporated herein by reference.

In one exemplary method, the effluent of the hydro-solvothermal reactor can be dried to form a powder. The dried powder can be suspended or dispersed in an organic solvent or water to which a surface modification agent has been added. The surface modification agent is selected to facilitate the dispersion of the tin oxide nanoparticles in the liquid medium.

In another example, the effluent of the continuous hydrothermal reactor can be treated with a surface modification agent before being dried to form a powder. The surface modification agent is added to the effluent of the hydro-solvothermal reactor. The surface modification agent is selected to facilitate the dispersion of the tin oxide nanoparticles into an organic matrix. The treated effluent is then dried to a powder. The dried powder can be suspended or dispersed in an organic matrix.

In some embodiments, the effluent from the hydro-solvothermal reactor is concentrated (but not dried to powder) to remove at least a portion of the aqueous based medium. This concentration process often removes at least a portion of the dissolved carboxylic acids and/or anions thereof. Optionally, additional dissolved carboxylic acid and/or anion thereof in the concentrate can be removed by a treatment such as dialysis, diafiltration, or ion-exchange. The concentrated and optionally treated tin oxide sol can be mixed with the surface modification agent and an optional organic solvent. After surface treatment, the surface modified tin oxide nanoparticle can be mixed with an organic matrix. The optional organic solvent and the remaining water can be removed before or after addition of the organic matrix. Alternatively, the concentrated tin oxide sol can be mixed with both the organic matrix and the surface modification agent in the presence or an optional organic solvent. The optional organic solvent and the remaining water can be removed after surface modification.

In another embodiment, the effluent from the hydro-solvothermal reactor is concentrated (but not dried to powder) to remove at least a portion of the aqueous based medium. This concentration process often removes at least a portion of the dissolved carboxylic acids and/or anions thereof. Optionally, additional dissolved carboxylic acid and/or anion thereof in the concentrate can be removed by a treatment such as dialysis, diafiltration, or ion-exchange. The concentrated and optionally treated tin oxide sol can be mixed with the surface modification agent. After surface treatment, the mixture can be dried to form a powder. This surface modified tin oxide nanoparticle powder can be dispersed in to an organic matrix.

The surface modification reactions can occur at room temperature (e.g., 20° C. to 25° C.) or at an elevated temperature (e.g., up to about 95° C.). When the surface modification agents are acids such as carboxylic acids, the doped and undoped tin oxide particles typically can be surface-modified at room temperature. When the surface modification agents are silanes, the doped and undoped tin oxide particles are typically surface modified at elevated temperatures.

The organic matrix typically includes a polymeric material or a precursor to a polymeric material (e.g., a monomer or an oligomer having a polymerizable group). Any suitable technique can be used to combine the doped and undoped tin oxide particles with the organic matrix. For example, if the organic matrix is a precursor to a polymeric material, the doped and undoped tin oxide particles can be added prior to the polymerization reaction. If the polymeric material is a thermoplastic, the polymeric material and the doped and undoped tin oxide particles can be combined using a process such as extrusion, milling, or Brabender mixing. The composite material containing a precursor of a polymeric material is often shaped or coated before polymerization.

Exemplary monomers include (meth)acrylate-based monomers, styrene-based monomers, and epoxy-based monomers. Exemplary reactive oligomers include polyesters having (meth)acrylate groups, polyurethanes having (meth) acrylate groups, and acrylics. Exemplary polymeric material include polyolefins, polyesters, polyurethanes, poly(meth) acrylates, polystyrenes, polycarbonates, and polyimides.

One exemplary process for suspending or dispersing the doped or undoped tin oxide nanoparticles in an organic matrix includes concentrating the effluent from the hydro-solvo thermal reactor using a method (e.g., distillation or rotary evaporation). A co-solvent and surface modification agent is then added to the concentrate. After addition of the organic matrix, the co-solvent, water, and at least a portion of the dissolved carboxylic acid and/or anion thereof are removed. In a more specific example, the surface modification agent is a carboxylic acid (e.g., a carboxylic acid having a polyalkylene oxide group) and the organic group and the organic matrix is the reaction product of at least one (meth)acrylate.

The total amount of the various salts dissolved in the feedstock can be readily determined based on the total percent solids selected for the feedstock. The relative amounts of the various salts can be calculated to provide the selected composition for the tin oxide-based particles.

In some embodiments, the crystalline, surface modified tin oxide nanoparticles comprise up to 20 (in some embodiments, up to 15, 10, 5, 4, 3, 2, 1, or even up to 0.5; in some embodiments, in a range from greater than zero to 20; 1 to 20, 5 to 20, or even 10 to 15) atom percent of dopant. Exemplary dopants include at least one of at least one of a metal or metal oxide of at least one of aluminum, gallium, antimony, indium, bismuth, lead, transition metal (i.e., Ti, V, Cr, Mn, Fe, Co, Ni, Cu, Zn, Zr, Nb, Mo, Ru, Rh, Pd, Ag, Cd, Hf, Ta, W, Re, Ir, Pt, and/or Au) or lanthanide (i.e., La, Ce, Pr, Nd, Sm, Eu, Gd, Tb, Dy, Ho, Er, Tm, Yb, and/or Lu). Doped tin oxides have different electronic properties than undoped tin oxide nanoparticles. For examples undoped tin dioxide is a wide band gap semiconductor whereas antimony doped tin dioxide is an electronically conducting material. Rare-earth doped tin oxide materials can exhibit fluorescence under ultraviolet excitation. Transition metal doped tin oxide can exhibit interesting magnetic properties. Silver, gold, palladium, platinum and other transition metal doped tin oxide nanoparticles can also have catalytic applications. Surface modified nanoparticle dispersions of these doped tin oxides can enable formation of bulk nanocomposites, nanocomposite coatings or films when combined with appropriate polymers or resins. Organocarboxylate modified doped tin oxide nanoparticles can be calcined to yield nanocrystalline ceramic coatings and high surface area powders. Nanocomposite and ceramic coatings formed from these surface modified doped tin oxide nanoparticles can also manifest the electronic property of the doped oxide in the final product (e.g., visible transparency and IR absorption property of the ATO nanoparticles is exhibited in the nanocomposites coatings formed by ATO nanoparticles when combined with appropriate resins).

A dispersion comprising plurality of crystalline, surface modified tin oxide nanoparticles can be prepared, for example, by providing a solution preparable by combining at least a tin carboxylate (e.g., tin acetate, tin formate, tin propionate, tin butanoate, tin pentanoate, and tin hexanoate), a dopant precursor comprising at least one of aluminum, gallium, antimony, indium, bismuth, lead, transition metals (i.e., Ti, V, Cr, Mn, Fe, Co, Ni, Cu, Zn, Zr, Nb, Mo, Ru, Rh, Pd, Ag, Cd, Hf, Ta, W, Re, Ir, Pt, and/or Au), or lanthanide (i.e., La, Ce, Pr, Nd, Sm, Eu, Gd, Tb, Dy, Ho, Er, Tm, Yb, and/or Lu), water, and carboxylic acid, to provide the solution, wherein a sufficient amount of water is present to dissolve the dopant precursor and metal carboxylate; and heating the solution to at least one temperature for a time sufficient to provide the crystalline, surface modified tin oxide nanoparticles. Exemplary liquid vehicles for dispersing the nanoparticles therein include organocarboxylic acid, alcohol, hydrocarbon solvents, ether, ketones, acrylate, methacrylate, and epoxy resin.

Crystalline, surface modified tin oxide nanoparticles described herein are useful, for example, for preparing transparent electrodes, conducting inks, IR absorbing transparent films and clear anti-static coatings. Lanthanide doped tin oxide nanoparticles can be used as fluorescent materials. Transition metal doped tin oxide nanoparticles can be used as heterogeneous catalysts.

Embodiments of crystalline, surface modified tin oxide nanoparticles described herein may also be useful in making gas sensor materials. Embodiments of surface modified antimony and/or indium doped tin oxide nanoparticles can enable formation of nanocomposite coatings or films when combined with compatible polymers or resins which can exhibit visible transparency and IR absorption property of antimony and/or indium doped tin dioxide nanoparticles.

Exemplary Embodiments

1. A plurality of crystalline, surface modified tin oxide nanoparticles, wherein the particles have a largest dimension up to 20 nm (in some embodiments, up to 15 nm, 10 nm, 5 nm, 3 nm, or even up to 2 nm; in some embodiments, in a range from 1 nm to 20 nm, 1 nm to 15 nm, 1 nm to 10 nm, 2 nm to 20 nm, 2 nm to 15 nm, 2 nm to 10 nm, 3 nm to 20 nm, 3 nm to 15 nm, or even 3 nm to 10 nm), and wherein the surface modifier comprises at least one of a organic carboxylic acid or anion thereof.

2. The plurality of crystalline, surface modified tin oxide nanoparticles of Embodiment 1, wherein the organic carboxylic acid comprises at least one polymerizable group.

3. The plurality of crystalline, surface modified tin oxide nanoparticles of either Embodiment 1 or 2, wherein the one organic carboxylic acid is selected from the group consisting of formic acid, acetic acid, propanoic acid, butanoic acid, and mixtures thereof.

4. The plurality of crystalline, surface modified tin oxide nanoparticles of any preceding Embodiment, wherein the surface modifier is at least one organic carboxylic acid.

5. The plurality of crystalline surface modified tin oxide nanoparticles of any preceding Embodiment further comprising a dopant comprising at least one of a metal or metal oxide of at least one of aluminum, gallium, antimony, indium, bismuth, lead, transition metal, or lanthanide.

6. The plurality of crystalline, surface modified tin oxide nanoparticles of Embodiment 5 comprising up to 20 (in some embodiments, up to 15, 10, 5, 4, 3, 2, 1, or even up to 0.5; in some embodiments, in a range from greater than zero to 20; 1 to 20, 5 to 20, or even 10 to 15) atom percent of the dopant.

7. The plurality of crystalline, surface modified tin oxide nanoparticles of any preceding Embodiment that are dispersible in at least one of water or organic solvent.

8. A dispersion comprising the plurality of crystalline, surface modified tin oxide nanoparticles of any preceding Embodiment.

9. The dispersion of Embodiment 8 that is a stable dispersion.

10. The dispersion of either Embodiment 8 or 9, wherein the plurality of crystalline, surface modified tin oxide nanoparticles are dispersed in at least one of organocarboxylic acid, alcohol, hydrocarbon solvents, ether, ketones, acrylate, methacrylate, or epoxy resin.

11. A method of making the plurality of crystalline, surface modified tin oxide nanoparticles of any of Embodiments 1 to 7, the method comprising:

providing a solution preparable by combining at least a tin carboxylate (e.g., tin formate, tin acetate, tin propionate, tin n-butyrate and tin iso-butyrate or a mixture thereof), a dopant precursor comprising at least one of aluminum, gallium, antimony, indium, bismuth, lead, transition metals (i.e., Ti, V, Cr, Mn, Fe, Co, Ni, Cu, Zn, Zr, Nb, Mo, Ru, Rh, Pd, Ag, Cd, Hf, Ta, W, Re, Ir, Pt, and/or Au), or lanthanide (i.e., La, Ce, Pr, Nd, Sm, Eu, Gd, Tb, Dy, Ho, Er, Tm, Yb, and/or Lu), water, and carboxylic acid, to provide the solution, wherein a sufficient amount of water is present to dissolve the dopant precursor and metal carboxylate; and heating the solution to at least one temperature for a time sufficient to provide the crystalline, surface modified tin oxide nanoparticles.

12. The method of Embodiment 11, wherein at least a portion of the heating is conducted in a range from 150° C. to 250° C. (in some embodiments, in a range from 150° C. to 250° C.).

13. The method of either Embodiment 11 or 12, wherein the water to tin carboxylate plus dopant mole ratio is in a range from 1.3:1 to 8.25:1 (in some embodiments, in a range from 2:1 to 8:1, 3:1 to 8:1, 4:1 to 8:1, 5:1 to 8:1, or even 6:1 to 7:1)

14. The method of any of Embodiments 11 to 13, wherein the carboxylic acid to water mole ratio is in a range from 2.8:1 to 15.6:1 (in some embodiments, in a range from 2:1 to 15:1, 2:1 to 13:1, 2:1 to 10:1, 2:1 to 8:1, 2:1 to 5:1, or even 3:1 to 4:1).

15. A method of making the plurality of crystalline, surface modified tin oxide nanoparticles of any of Embodiments 1 to 7, the method comprising:

providing a solution preparable by combining at least a tin carboxylate water, and carboxylic acid, wherein the carboxylic acid to water mole ratio is at least 2:1 (in some embodiments, at least 3:1, 4:1, 5:1, 10:1, or even at least 15:1; in some embodiments, in a range from 3.5:1 to 1.5:1), and wherein the water to tin carboxylate plus dopant mole ratio is at least 1.3:1 (in some embodiments, at least 2:1, 3:1, 4:1, 5:1, or even at least 8:1; in some embodiments, in a range from 1.3:1 to 8.25:1) and heating the solution to at least one temperature for a time sufficient to provide the crystalline, surface modified tin oxide nanoparticles.

16. The method of Embodiment 15, wherein at least a portion of the heating is conducted in a range from 150° C. to 250° C. (in some embodiments, in a range from 150° C. to 250° C.).

17. The method of any of either Embodiment 15 or 16, wherein the carboxylic acid to water mole ratio is in a range from 2.8:1 to 15.6:1 (in some embodiments, in a range from 2:1 to 15:1, 2:1 to 13:1, 2:1 to 10:1, 2:1 to 8:1, 2:1 to 5:1, or even 3:1 to 4:1).

Advantages and embodiments of this invention are further illustrated by the following examples, but the particular materials and amounts thereof recited in these examples, as well as other conditions and details, should not be construed to unduly limit this invention.

All chemicals and reagents were used without further purification unless noted otherwise. Antimony III acetate 97% and tin (IV) acetate (I) were obtained from Alfa Aesar, Ward Hill, Mass., unless indicated otherwise. Copper (II) acetate monohydrate 98%, and nickel (II) acetate tetrahydrate 98%, Oleic acid 90%, 2-[2-(2-methoxyethoxy)ethoxy]acetic acid (MEEAA), mono-2-(methacryloyloxy)ethyl succinate, 1-methoxy 2-propanol and heptane were obtained from Sigma-Aldrich, Milwaukee, Wis. 1,6 hexanediol diacrylate and polyethylene glycol (600) diacrylate, both reactive bifunctional monomers were obtained under the trade designations "SR-238B" and "SR-610", respectively, from Sartomer, Exton, Pa. Dysprosium acetate hydrate was obtained from Gelest Inc., Morrisville, Pa. Glacial acetic acid, 99.7% manufactured by BDH/Aristar was obtained from VWR International Inc., West Chester, Pa. 1-hydroxy-cyclohexyl-phenyl ketone, an ultraviolet photo initiator, was obtained under the trade designation "IRGACURE 184" from Ciba Specialties, Hawthorne, N.Y.

Test Methods

X-Ray Diffraction (XRD)

Reflection geometry data were collected in the form of a survey scan using a vertical diffractometer (obtained from Panalytical, Westborough, Mass.) with copper $K_\alpha$ radiation, and proportional detector registry of the scattered radiation. The diffractometer was fitted with variable incident beam slits, fixed diffracted beam slits, and graphite diffracted beam monochromator. The survey scan was conducted from 5 to 80 degrees (2θ) using a 0.04 degree step size and 4 second dwell time. X-ray generator settings of 45 kV and 35 mA were employed. Samples were examined as dry powders and placed on zero background specimen holders. Diffraction patterns were identified using reference patterns contained within the International Centre for Diffraction Data (ICDD), Newtown Square, Pa., powder diffraction file and use of X-ray diffraction analysis software obtained under the trade designation "JADE" (version 9.1) from MDI, Livermore, Calif.

Apparent Crystallite Size Evaluation from XRD Data

Observed diffraction peaks were subjected to profile fitting using a Pearson VII peak shape model, cubic spline background model, and X-ray diffraction analysis software ("JADE"; v. 9.1). Peak widths were taken as the full width at half maximum (FWHM) of the $K_{\alpha 1}$ component. Apparent crystallite sizes ($D_{app}$) were determined using the Scherrer equation and observed peak FWHM values after corrections for instrumental broadening and employing a shape factor of 0.9.

$D_{app} = K\lambda/\beta \cos(\theta)$ (result in Å)  Scherrer equation where:

K=0.90 (shape factor)
λ=1.540598 Å wavelength Cu $K_{\alpha 1}$
β=peak FWHM value (in radians) after correction for instrumental broadening
θ=half of the peak position 2θ

Further details on the Scherrer equation can be found, for example, in *X-ray Diffraction Procedures for Polycrystalline and Amorphous Materials*, Harold P. Klug and Leroy E. Alexander, Published by John Wiley & Sons, Inc., New York (1954), Chapter 9, p. 491 and P. Scherrer, *Göttinger Nachrichten*, 2, p. 98 (1918).

Thermogravimetric Analysis (TGA)

The weight loss of the solids was performed dried sols using thermogravimetric analysis (TGA) equipment (obtained under the trade designation "TGA Q500" from TA Instruments, New Castle, Del.). The sols were dried at 120° C. to yield a dry solid. The following temperature profile was used with the TGA equipment; (1) Equilibrated at 85° C.; (2) Ramped at 20° C./min. to 200° C.; (3) held at 200° C. for 20 min., and (4) Ramped at 20° C./min to 900° C. The weight loss above 200° C. was taken to be weight loss of any bound acid, water or further chemical reactions.

Example 1

A precursor solution (7 wt. % as oxide) was prepared by mixing to a vial 1 gram of tin IV acetate and 4.6 grams of acetic acid, and 0.37 gram of deionized water. The vial was then warmed in a 65° C. water bath until a clear stable solution was obtained. The mole percent ratio of dopant to tin is listed in the Table, below.

TABLE

| | Dopant:Sn, mole % | TGA %, 900° C. Residue | XRD Crystal Size, nm |
|---|---|---|---|
| 1 | 0/100 | 88.3 | 3.9 |
| 2 | 5/95 | 90.7 | 4.1 |
| 3 | 10/90 | 90.2 | 3.6 |
| 4 | 15/85 | 89.0 | 3.5 |
| 5 | 20/80 | 89.3 | 3.3 |
| 6 | 30/70 | 90.5 | 3.0 |
| 7 | 10/90 | 89.6 | 3.8 |
| 8 | 5/95 | 86.7 | 3.4 |
| 9 | 5/95 | 86.8 | 3.3 |
| 10 | 5/95 | 84.6 | 3.3 |
| 12 | 15/85 | 86.6 | — |
| 13 | 15/85 | 89.2 | — |
| 14 | 15/85 | 91.6 | — |
| 15 | 15/85 | 84.5 | — |
| 16 | 15/85 | 86.3 | — |

Six grams of this precursor solution was poured in to a polytetrafluoroethylene (PTFE) cup which was then placed in a 23 ml general purpose acid digestion bomb (obtained as Model 4749 from Parr Instrument Company, Moline, Ill.) and tightly sealed. The acid digestion bomb was placed in a convection oven set at 225° C. for 4 hours. The acid digestion bomb was cooled by quenching it in cold water. The resulting product was a clear and stable colorless dispersion that had no settled material visible. No settling was observed after 4 days. After drying the dispersion in oven at 120° C. for 30 minutes, the solid content of the sol was determined to be 8.5 wt. %. The dried powder sample obtained was analyzed by XRD and TGA and results are summarized in the Table, above.

Example 2

A precursor solution (7 wt. % as oxide) was prepared by mixing in a first vial 0.09 gram of antimony III acetate;

inductively coupled plasma (ICP) analysis listed Sb at 40.0%) and 4.8 grams of acetic acid. The vial was warmed in a 65° C. water bath until a solution was obtained.

To a second vial, 2 grams of tin IV acetate (ICP analysis listed Sn at 31.9%), 4.8 grams of acetic acid and 0.78 gram of deionized water were added. The vial was then warmed in a 65° C. water bath until a solution was obtained.

The first vial was then poured into the second vial, and a clear stable yellow solution was obtained. The Sb:Sn atomic ratio was 5:95.

Ten grams of the resulting precursor solution was heated and then cooled as described in Example 1. The resulting product was a cloudy dispersion when mixed. After standing for 4 days a clear and stable dark blue-green dispersion with some settled material at the bottom (<5 wt. % of total solids in the product) was obtained. The solid content measured was 7.9 wt. % after drying the clear dispersed portion of the product, and analyzing the resulting powder as described in Example 1. Results are summarized in the Table, above.

Example 3

A precursor solution (7 wt. % as oxide) was prepared by mixing in a first vial 0.19 gram of antimony III acetate and 5 grams of acetic acid. The vial was then warmed in a 65° C. water bath until in solution was obtained.

To a second vial, 2 grams of tin IV acetate, 5 grams of acetic acid, and 0.82 gram of deionized water were added. The vial was then warmed in a 65° C. water bath until a solution was obtained.

The first vial was then poured into the second vial, and a clear stable yellow solution was obtained. The Sb:Sn atomic ratio was 10:90.

Ten grams of the resulting precursor solution was heated and then cooled as described in Example 1. The resulting product was a cloudy dispersion when mixed. After standing for 4 days a clear and stable dark blue-green dispersion with some settled material at the bottom (<5 wt. % of total solids in the product) was obtained. The solid content measured was 8 wt. % after drying the clear dispersed portion of the product, and analyzing the resulting powder as described in Example 1. Results are summarized in the Table, above.

Example 4

A precursor solution (7 wt. % as oxide) was prepared by mixing in a first vial 0.3 gram of antimony III acetate and 5.3 grams of acetic acid. The vial was then warmed in a 65° C. water bath until a solution was obtained.

To a second vial, 2 grams of tin IV acetate, 5.3 grams of acetic acid, and 0.86 gram of deionized water were added. The vial was then warmed in a 65° C. water bath until a solution was obtained.

The first vial was then poured to the second vial and a clear stable yellow solution was obtained. The Sb:Sn atomic ratio was 15:85.

Ten grams of the resulting precursor solution was heated and then cooled as described in Example 1. The resulting product was a clear and stable dark blue-green dispersion that had no settled material visible. No settling was observed after 4 days. The solid content measured was 8.2 wt. % after drying the dispersion, and analyzing the resulting powder as described in Example 1. Results are summarized in the Table, above.

Example 5

A precursor solution (7 wt. % as oxide) was prepared by mixing in a first vial 0.42 gram of antimony III acetate and 5.6 grams of acetic acid. The vial was then warmed in a 65° C. water bath until in solution was obtained.

To a second vial, 2 grams of tin IV acetate, 5.6 grams of acetic acid, and 0.9 gram of deionized water were added. The vial was then warmed in a 65° C. water bath until a solution was obtained.

The first vial was then poured to the second vial, and a clear stable yellow solution obtained. The Sb:Sn atomic ratio was 20:80.

Ten grams of the resulting precursor solution was heated and then cooled as described in Example 1. The resulting product was a clear and stable dark blue-green dispersion that had no settled material visible. No settling was observed after 4 days. The solid content measured was 8.2 wt. % after drying the dispersion, and analyzing the resulting powder as described in Example 1. Results are summarized in the Table, above.

Example 6

A precursor solution (7 wt. % as oxide) was prepared by mixing in a first vial 0.72 gram of antimony III acetate and 6.3 grams of acetic acid. The vial was then warmed in a 65° C. water bath until in solution was formed.

To a second vial, 2 grams of tin IV acetate, 6.3 grams of acetic acid, and 1 gram of deionized water were added. The vial was then warmed in a 65° C. water bath until in solution.

The first vial was then poured into the second vial and a clear stable yellow solution was obtained. The Sb:Sn atomic ratio was 30:70.

Ten grams of the resulting precursor solution was heated and then cooled as described in Example 1. The resulting product was a cloudy dispersion. After standing for 4 days a clear and stable dark blue-green dispersion with some settled material at the bottom (<5 wt. % of total solids in the product) was obtained. The solid content measured was 8.2 wt. % after drying the clear dispersed portion of the product, and analyzing the resulting powder as described in Example 1. Results are summarized in the Table, above.

Example 7

A precursor solution (7.9 wt. % as oxide) was prepared by mixing in to a first vial 0.17 gram of antimony III acetate and 4.4 grams of acetic acid. The vial was then warmed in a 65° C. water bath until a solution was formed.

To a second vial, 1.75 gram of tin IV acetate (obtained from Sigma-Aldrich, Milwaukee, Wis.), 4.4 grams of acetic acid, and 0.7 gram of deionized water were added. The vial was then warmed in a 65° C. water bath until a solution was formed.

The first vial was then poured into the second vial and a cloudy yellow solution obtained with some settling. The Sb:Sn atomic ratio was 10:90.

Eleven grams of the resulting precursor solution was heated and then cooled as described in Example 1. The resulting product was a clear and stable dark blue-green dispersion that had no settled material visible. No settling was observed after 4 days. The solid content measured was 8.7 wt. % after drying the dispersion, and analyzing the powder as described in Example 1. Results are summarized in the Table, above.

Example 8

A precursor solution (7.5 wt. % as oxide) was prepared by mixing in a first vial 0.06 gram of copper II acetate monohydrate and 4.4 grams of acetic acid. The vial was then warmed in a 65° C. water bath until a solution was obtained.

To a second vial, 1.75 gram of tin IV acetate (obtained from obtained from Sigma-Aldrich, Milwaukee, Wis.), 4.4 grams of acetic acid, and 0.7 gram of deionized water were added. The vial was then warmed in a 65° C. water bath until a solution was formed.

The first vial was then poured to the second vial and a cloudy blue/green solution was obtained with some settling. The Cu:Sn atomic ratio was 5:95.

Eleven grams of the resulting precursor solution was heated and then cooled as described in Example 1. The resulting product was a cloudy dispersion. After standing for 4 days a clear and stable sea green sol with some settled material at the bottom (<5 wt. % of total solids in the product) was obtained. The solid content measured was 8.5 wt. % after drying the clear dispersed portion of the product, and analyzing the resulting powder as described in Example 1. Results are summarized in the Table, above.

Example 9

A precursor solution (7.4 wt. % as oxide) was prepared by mixing in a first vial 0.07 gram of nickel II acetate tetrahydrate and 4.4 grams of acetic acid. The vial was then warmed in a 65° C. water bath until a solution was obtained.

To a second vial, 1.75 gram of tin IV acetate (obtained from obtained from Sigma-Aldrich, Milwaukee, Wis.), 4.4 grams of acetic acid, and 0.7 gram of deionized water were added. The vial was then warmed in a 65° C. water bath until a solution was obtained.

The first vial was then poured into the second vial and a cloudy blue/green solution obtained with some settling. The Ni:Sn atomic ratio was 5:95.

Eleven grams of the resulting precursor solution was heated and then cooled as described in Example 1. The resulting product was a clear and stable light lime-green dispersion that had no settled material visible. No settling was observed after 4 days. The solid content measured was 8.4 wt. % after drying the dispersion, and analyzing the resulting powder as described in Example 1. Results are summarized in the Table, above.

Example 10

A precursor solution (7.9 wt. % as oxide) was prepared by mixing in a first vial 0.2 gram of dysprosium acetate hydrate, 4.4 grams of acetic acid and 0.2 gram of deionized water. The vial was then warmed in a 65° C. water bath until a solution was obtained.

To a second vial, 1.75 gram of tin IV acetate (obtained from Sigma-Aldrich, Milwaukee, Wis.), 4.4 grams of acetic acid, and 0.7 gram of deionized water were added. The vial was then warmed in a 65° C. water bath until a solution was obtained.

The first vial was then poured into the second vial and a cloudy solution was obtained with some settling. The Dy:Sn atomic ratio was 5:95.

Eleven grams of the resulting precursor solution was heated and then cooled as described in Example 1. The resulting product was a clear and stable colorless dispersion without any settling. No settling was observed after 4 days. The solid content measured was 9.2 wt. % after drying the dispersion, and analyzing the resulting powder as described in Example 1. Results are summarized in the Table, above.

Example 11

A precursor solution (7.5 wt. % as oxide) was prepared by mixing in a first vial 0.4225 gram of antimony III acetate and 5.6 grams of acetic acid. The vial was then warmed in a 65° C. water bath until a solution was obtained.

To a second vial, 2 grams of tin IV acetate and 5.6 grams of acetic acid (no deionized water) were added to the vial. The vial was then warmed in a 65° C. water bath but did not go into solution.

The second vial was then poured to the second vial, but a solution was not obtained. The Sb:Sn atomic ratio was 10:90.

Ten grams of the resulting precursor solution was heated and then cooled as described in Example 1. The resulting product was a soft solid plug of needle like solids with some dark blue solution surrounding.

Example 12

A precursor solution (6.9 wt. % as oxide) was prepared by mixing in a first vial 0.27 gram of antimony III acetate and 4.8 grams of acetic acid. The vial was then warmed in a 65° C. water bath until a solution was obtained.

To a second vial, 2 grams of tin IV acetate and 4.8 grams of acetic acid and 0.8 gram of deionized water were added. The vial was then warmed in a 65° C. water bath until a solution was obtained.

The first vial was then poured to the second vial and a clear solution was obtained. The Sb:Sn atomic ratio was 15:85.

12.5 grams of the resulting precursor solution was heated and then cooled as described in Example 1. The resulting product was a clear and stable dark green-blue dispersion without any settling. No settling was observed after 4 days. The solid content measured was 8.3 wt. % after drying the dispersion, and analyzing the resulting powder by TGA as described in Example 1. Results are summarized in the Table, above.

Example 13

A precursor solution (6.9 wt. % as oxide) was prepared by mixing in a first vial 0.27 gram of antimony III acetate and 4.4 grams of acetic acid. The vial was then warmed in a 65° C. water bath until a solution was obtained.

To a second vial, 2 grams of tin IV acetate and 4.4 grams of acetic acid and 1.6 gram of deionized water were added. The vial was then warmed in a 65° C. water bath to obtain a clear solution with gel like solids.

The first vial was then poured to the second vial and a clear solution was obtained along with gel-like solids. The Sb:Sn atomic ratio was 15:85.

12.5 grams of the resulting precursor was heated and then cooled as described in Example 1. The resulting product was a dark green-blue dispersion with gel-like solids. After standing for 4 days a clear and stable dark green-blue sol with some settled material at the bottom was obtained. The solid content measured (by method as described in Example 1) was 8.3 wt. % after drying the clear dispersed portion of the product and 8.4 wt. % from the dispersed product including the settled material. The powder obtained from drying the clear dispersed portion of the product was further analyzed by TGA as described in Example 1. Results are summarized in the Table, above.

Example 14

A precursor solution (7.1 wt % as oxide) was prepared by mixing in a first vial 0.27 gram of antimony III acetate and 2.4 grams of acetic acid and 2.7 grams of 1-methoxy-2-propanol. The vial was then warmed in a 65° C. water bath until a solution was obtained.

To a second vial, 2 grams of tin IV acetate and 2.4 grams of acetic acid and 2.7 grams of 1-methoxy-2-propanol and 0.25 gram of deionized water were added. The vial was then warmed in a 65° C. water bath until a solution was obtained.

The first vial was then poured to the second vial and a clear solution was obtained. The Sb:Sn atomic ratio is 15:85.

12.4 grams of the resulting precursor solution was heated and then cooled as described in Example 1. The resulting product was a soft gel that is gray-blue-green in color and on agitating yields an opaque solution with settling. The solid content measured was 7.5 wt. % after drying the dispersed portion of the product, and analyzing the resulting powder by TGA as described in Example 1. Results are summarized in the Table, above.

Example 15

A precursor solution (6.9 wt % as oxide) was prepared by mixing in a first vial (A) 0.27 gram of antimony III acetate and 5.3 grams of acetic acid. The vial was then warmed in a 65° C. water bath until a solution was obtained.

To a second vial, 2 grams of tin IV acetate and 4.8 grams of acetic acid and 0.25 gram of deionized water were added. The vial was then warmed in a 65° C. water bath until a solution was obtained.

The first vial was then poured to the second vial and a clear solution was obtained. The Sb:Sn atomic ratio was 15:85.

12.5 grams of the precursor solution was heated and then cooled as described in Example 1. The resulting product was a cloudy dark green-blue dispersion. After standing for 4 days a clear and stable dark green-blue sol with some settled material as the bottom was obtained. The solid content measured (by method as described in Example 1) was 8.7 wt % after drying the clear dispersed portion of the product and 9.1 wt. %, from the dispersed product including the settled material. The powder obtained from drying the clear dispersed portion of the product was further analyzed by TGA as described in Example 1. Results are summarized in the Table, above.

Example 16

A precursor solution (6.9 wt. % as oxide) was prepared by mixing in a first vial 0.27 gram of antimony III acetate and 5.1 grams of acetic acid. The vial was then warmed in a 65° C. water bath until a solution was obtained.

To a second vial 2 grams of tin IV acetate, 4.8 grams of acetic acid and 0.45 gram deionized water were added. The vial was then warmed in a 65° C. water bath until a solution was obtained.

The first vial was then poured into the second vial and a clear solution was obtained. The Sb:Sn atomic ratio was 15:85.

12.5 grams of the resulting precursor solution was heated and then cooled as described in Example 1. The resulting product was a cloudy dark green-blue dispersion. After standing for 4 days a clear and stable dark green-blue sol with some settled material as the bottom was obtained. The solid content measured (by method as described in Example 1) was 8.6 wt. % after drying the clear dispersed portion of the product and 8.9 wt. %, from the dispersed product including the settled material as described in Example 1. The powder obtained from drying the clear dispersed portion of the product was further analyzed by TGA as described in Example 1. Results are summarized in the Table, above.

Example 17

1 gram of dispersion from Example 12 was mixed with 0.03 gram of MEEAA in a vial. The mixture was then poured in a glass petri dish and heated in an oven set at 90° C. for 30 minutes. The resulting dried powder forms a stable dark blue-green dispersion in 1-methoxy 2-propanol with no settling.

Example 18

2 grams of dispersion from Example 12 was mixed with 0.02 gram of MEEAA and 0.02 gram of mono-2-(methacryloyloxy)ethyl succinate in a vial. The mixture was then poured in a glass petri dish and heated as in Example 17. The resulting dried powder forms a stable blue-green dispersion in 1-methoxy 2-propanol with no settling.

Example 19

1 gram of dispersion obtained in Example 8 was mixed with 0.03 gram of MEEAA in a vial. The mixture was then poured in a glass petri dish and heated as in Example 17. The resulting dried powder forms a light green dispersion in 1-methoxy 2-propanol with no settling.

Example 20

1 gram of dispersion from Example 10 was mixed with 0.03 gram of MEEAA in a vial. The mixture was then poured in a glass petri dish and heated as in Example 17. The resulting dried powder forms a colorless dispersion in 1-methoxy 2-propanol with no settling.

Example 21

0.12 gram of dispersion from Example 18 was mixed with 0.13 gram of polyethylene glycol (600) diacrylate ("SR-610"), 0.11 gram 1-methoxy 2-propanol, and 0.02 gram MEEAA in a vial and warmed in a water bath until a blue-green solution with no settling was obtained.

Example 22

0.11 gram of dispersion obtained in Example 18 was mixed with 0.15 gram of 1-methoxy 2-propanol, 0.03 gram MEEAA, and 0.13 gram of 1,6 hexanediol diacrylate ("SR-238B") in a vial and warmed in a water bath until a blue-green solution with no settling was obtained.

Example 23

0.5 gram of dispersion obtained in Example 12 was mixed with 0.05 gram of oleic acid and 0.5 gram of heptane in a vial. The mixture was then poured in a glass petri dish and heated on a warm hot plate until dry. The resulting powder forms a blue-green dispersion in heptane with no settling.

Example 24

1 gram of dispersion obtained in Example 18 was mixed with 0.5 gram of 1-methoxy 2-propanol, 0.8 gram of 1,6 hexanediol diacrylate ("SR-238B") and 0.026 gram of a photo initiator ("IRGACURE 184") to form a stable blue-green dispersion.

A drop of the sample was placed on to a glass slide and UV cured in a box under $N_2$ atmosphere with a germicidal lamp (25 watt, 254 nm wavelength; obtained from Sanyo Denko, Japan, under trade designation "G25T8") for 30 minutes. A clear film with a blue tint was obtained.

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. A method of making the plurality of crystalline, surface modified tin oxide nanoparticles, wherein the particles have a largest dimension up to 20 nm, the method comprising:
    combining at least a tin carboxylate, a dopant precursor, water, and a surface modifier, to provide a solution, wherein a sufficient amount of water is present to dissolve the dopant precursor and tin carboxylate, and wherein the surface modifier comprises at least one of an organic carboxylic acid or anion thereof; and
    heating the solution to at least one temperature for a time sufficient to provide the crystalline, surface modified tin oxide nanoparticles.

2. The method of claim 1, wherein the organic carboxylic acid comprises at least one polymerizable group.

3. The method of claim 1, wherein the one organic carboxylic acid is selected from the group consisting of formic acid, acetic acid, propanoic acid, butanoic acid, and mixtures thereof.

4. The method of claim 1, wherein the surface modifier is at least one organic carboxylic acid.

5. The method of claim 1, wherein the plurality of crystalline surface modified tin oxide nanoparticles comprise a dopant at least one of a metal or metal oxide of at least one of aluminum, gallium, antimony, indium, bismuth, lead, transition metal, or lanthanide.

6. The method of claim 5, wherein the plurality of crystalline surface modified tin oxide nanoparticles comprise up to 20 atom percent of the dopant.

7. The method of claim 1, wherein the dopant precursor comprises at least one of aluminum, gallium, antimony, indium, bismuth, lead, transition metals, or lanthanide.

8. The method of claim 1, wherein at least a portion of the heating is conducted in a range from 150° C. to 250° C.

9. The method of claim 1, wherein the carboxylic acid to water mole ratio is at least 2:1.

10. The method of claim 1, wherein the carboxylic acid to water mole ratio is in a range from 2.8:1 to 15.6:1.

11. The method of claim 1, wherein the water to tin carboxylate plus dopant mole ratio is at least 1.3:1.

12. The method of claim 1, wherein the water to tin carboxylate plus dopant mole ratio is in a range from 1.3:1 to 8.25:1.

* * * * *